(12) United States Patent
Hopkins et al.

(10) Patent No.: US 7,775,780 B2
(45) Date of Patent: Aug. 17, 2010

(54) SURGICAL CASSETTE

(75) Inventors: Mark A. Hopkins, Mission Viejo, CA (US); Kamran Salari, Irvine, CA (US); David L. Williams, Newport Beach, CA (US)

(73) Assignee: Alcon, Inc., Hunenberg (CH)

( * ) Notice: Subject to any disclaimer, the term of this patent is extended or adjusted under 35 U.S.C. 154(b) by 766 days.

(21) Appl. No.: 11/338,491

(22) Filed: Jan. 24, 2006

(65) Prior Publication Data

US 2007/0172368 A1    Jul. 26, 2007

(51) Int. Cl.
F04B 43/12    (2006.01)

(52) U.S. Cl. .................... 417/477.2; 604/153

(58) Field of Classification Search .......... 604/153, 604/131–132, 151; 417/477.2, 477.3, 202, 417/474, 476, 477.12, 477.13, 477.9
See application file for complete search history.

(56) References Cited

U.S. PATENT DOCUMENTS

| | | | |
|---|---|---|---|
| 4,140,118 A | 2/1979 | Jassawalla | |
| 4,187,057 A | 2/1980 | Xanthopoulos | |
| 4,479,761 A | 10/1984 | Bilstad et al. | |
| 4,493,706 A | 1/1985 | Borsanyi et al. | |
| 4,494,285 A | 1/1985 | O'Boyle | |
| 4,530,647 A | 7/1985 | Uno | |
| 4,537,561 A | 8/1985 | Xanthopoulos | |
| 4,657,490 A | 4/1987 | Abbott | |
| 4,713,051 A | 12/1987 | Steppe et al. | |
| 4,758,238 A | 7/1988 | Sundblom et al. | |
| 4,768,547 A | 9/1988 | Danby et al. | |
| 4,795,440 A | 1/1989 | Young et al. | |
| 4,798,090 A | 1/1989 | Heath et al. | |
| 4,798,580 A | 1/1989 | DeMeo et al. | |
| 4,838,865 A | 6/1989 | Flank et al. | |
| 4,861,242 A | 8/1989 | Finsterwald | |
| 4,886,431 A * | 12/1989 | Soderquist et al. | 417/477.2 |
| 4,904,168 A | 2/1990 | Cavoto et al. | |
| 4,921,477 A | 5/1990 | Davis | |
| 4,923,375 A | 5/1990 | Ejlersen | |
| 4,927,411 A | 5/1990 | Pastrone et al. | |
| 4,935,005 A | 6/1990 | Haines | |
| 4,963,131 A | 10/1990 | Wortrich | |

(Continued)

FOREIGN PATENT DOCUMENTS

DE    3542454    6/1987

(Continued)

*Primary Examiner*—Nicholas D Lucchesi
*Assistant Examiner*—Theodore J Stigell

(57) ABSTRACT

A cassette having an elastomeric sheet that is bonded or mechanically attached to a rigid substrate. A flow channel is molded into the rigid substrate that corresponds to a flow channel molded into the elastomeric sheet. The cassette is used in combination with a peristaltic pump having pump head rollers that are mounted radially from the axis of rotation of the pump motor so as to compress the elastomeric flow channels against the rigid substrate during operation. The flow channels molded into the rigid substrate have smooth, fluid lines free from sharp edges and abrupt direction changes and correspond with the fluid channels molded into the elastomeric sheet so as to provide a transition region with a relatively constant cross-section over its entire length that approximates the cross-sectional area of the flow channels molded into the rigid substrate and the fluid channel molded into the elastomeric sheet so that the entire fluid path is of relatively constant cross-sectional area.

18 Claims, 2 Drawing Sheets

U.S. PATENT DOCUMENTS

| | | |
|---|---|---|
| 5,041,096 A | 8/1991 | Beuchat et al. |
| 5,056,992 A | 10/1991 | Simons et al. |
| 5,106,366 A | 4/1992 | Steppe |
| 5,195,960 A | 3/1993 | Hossain et al. |
| 5,207,647 A | 5/1993 | Phelps |
| 5,267,956 A | 12/1993 | Beuchat |
| 5,302,093 A | 4/1994 | Owens et al. |
| 5,364,342 A | 11/1994 | Beuchat et al. |
| 5,403,277 A | 4/1995 | Dodge et al. |
| 5,429,485 A | 7/1995 | Dodge |
| 5,429,602 A | 7/1995 | Hauser |
| 5,460,490 A | 10/1995 | Carr et al. |
| 5,470,312 A | 11/1995 | Zanger et al. |
| 5,518,378 A | 5/1996 | Neftel et al. |
| 5,588,815 A | 12/1996 | Zaleski, II |
| 5,634,907 A | 6/1997 | Rani et al. |
| 5,709,539 A | 1/1998 | Hammer et al. |
| 5,746,708 A | 5/1998 | Giesler et al. |
| 5,746,719 A | 5/1998 | Farra et al. |
| 5,759,017 A | 6/1998 | Patton et al. |
| 5,810,204 A | 9/1998 | Devlin et al. |
| 5,897,524 A | 4/1999 | Wortrich et al. |
| 5,906,598 A | 5/1999 | Gielser et al. |
| 5,910,110 A | 6/1999 | Bastable |
| 5,927,956 A | 7/1999 | Lim et al. |
| 5,996,634 A | 12/1999 | Dennehey et al. |
| 6,012,999 A | 1/2000 | Patterson |
| 6,059,544 A | 5/2000 | Jung et al. |
| 6,129,699 A | 10/2000 | Haight et al. |
| 6,293,926 B1 * | 9/2001 | Sorensen et al. ............ 604/153 |
| 6,364,857 B1 | 4/2002 | Gray et al. |
| 6,561,999 B1 | 5/2003 | Nazarifar et al. |
| 6,572,349 B2 | 6/2003 | Sorensen et al. |
| 6,811,386 B2 | 11/2004 | Hedington et al. |
| 6,962,488 B2 | 11/2005 | Davis et al. |
| 7,393,189 B2 | 7/2008 | Davis et al. |
| 2003/0225363 A1 | 12/2003 | Gordon et al. |
| 2005/0186098 A1 | 8/2005 | Davis et al. |
| 2005/0245888 A1 | 11/2005 | Cull |
| 2007/0005030 A1 | 1/2007 | Hopkins et al. |
| 2007/0107490 A1 | 5/2007 | Artsyukhovich et al. |
| 2007/0207041 A1 | 9/2007 | Gao et al. |
| 2007/0219494 A1 | 9/2007 | Gao et al. |
| 2008/0125694 A1 | 5/2008 | Domash |
| 2008/0200878 A1 | 8/2008 | Davis et al. |

FOREIGN PATENT DOCUMENTS

| | | |
|---|---|---|
| DE | 19529894 A1 | 8/1995 |
| DE | 195 29 894 | 2/1997 |
| EP | 0870925 A2 | 10/1998 |
| EP | 0870925 B1 | 10/1998 |
| EP | 1099854 A1 | 5/2001 |
| EP | 1810702 A1 | 7/2007 |
| EP | 1810702 B1 | 10/2008 |
| FR | 2 466 641 A | 4/1981 |
| WO | WO 93/18802 | 9/1993 |

* cited by examiner

SURGICAL CASSETTE

BACKGROUND OF THE INVENTION

The present invention relates generally to peristaltic pumps and more specifically to peristaltic pumps used in ophthalmic surgical equipment.

Most prior art peristaltic pumps work by compressing or squeezing a length of flexible tubing (sometimes between a fixed race) using a rotating roller head. As the roller head rotates, the rollers pinch off a portion of the tubing and push any fluid trapped in the tubing between the rollers in the direction of rotation. Peristaltic pumps are widely used in medical applications because of their predictable, constant flow properties. These prior art systems, however, typically require manual connection of the pump tube segment around the rotating roller head.

Prior art peristaltic pumps using rotating roller heads also typically impart unwanted pressure pulsations. Several pulsation damping devices have been developed to address this problem (see e.g., U.S. Pat. No. 4,921,477 (Davis)).

Some prior art cassettes have tapered sections of pump tube so that the compression of the tube is more gradual and less abrupt. See for example U.S. Pat. No. 6,293,926 B1 (Sorensen, et al.). This tapering of the pump tubing has helped reduce pressure pulsations, but additional reduction is desirable.

Accordingly, a need continues to exist for a peristaltic pump that reduces pressure pulsations.

BRIEF SUMMARY OF THE INVENTION

The present invention improves upon prior art peristaltic pump cassettes by providing a cassette having an elastomeric sheet that is bonded or mechanically attached to a rigid substrate. A flow channel is molded into the rigid substrate that corresponds to a flow channel molded into the elastomeric sheet. The cassette is used in combination with a peristaltic pump having pump head rollers that are mounted radially from the axis of rotation of the pump motor so as to compress the elastomeric flow channels against the rigid substrate during operation. The flow channels molded into the rigid substrate have smooth, fluid lines free from sharp edges and abrupt direction changes and correspond with the fluid channels molded into the elastomeric sheet so as to provide a transition region with a relatively constant cross-section over its entire length that approximates the cross-sectional area of the flow channels molded into the rigid substrate and the fluid channel molded into the elastomeric sheet so that the entire fluid path is of relatively constant cross-sectional area.

One objective of the present invention is to provide a cassette that uses molded elastomeric flow channels.

Another objective of the present invention is to provide a cassette for a peristaltic pump having radially oriented pump rollers.

Yet another objective of the present invention is to provide a cassette for a peristaltic pump having pump rollers that compress elastomeric flow channels in the cassette against a rigid substrate.

Still another objective of the present invention is to provide a cassette having fluid channels molded into a rigid substrate, the flow channels having smooth, fluid lines free from sharp edges and abrupt direction changes.

Still another objective of the present invention is to provide a cassette having fluid channels molded into a rigid substrate, the flow channels correspond with fluid channels molded into an elastomeric sheet so as to provide a flow channel with a relatively constant cross-section over its entire length.

Yet another objective of the present invention is to provide a cassette have a fluid pathway that is of relatively constant cross-sectional area.

These and other advantages and objectives of the present invention will become apparent from the detailed description, drawings and claims that follow.

DETAILED DESCRIPTION OF THE INVENTION

Figure 1:
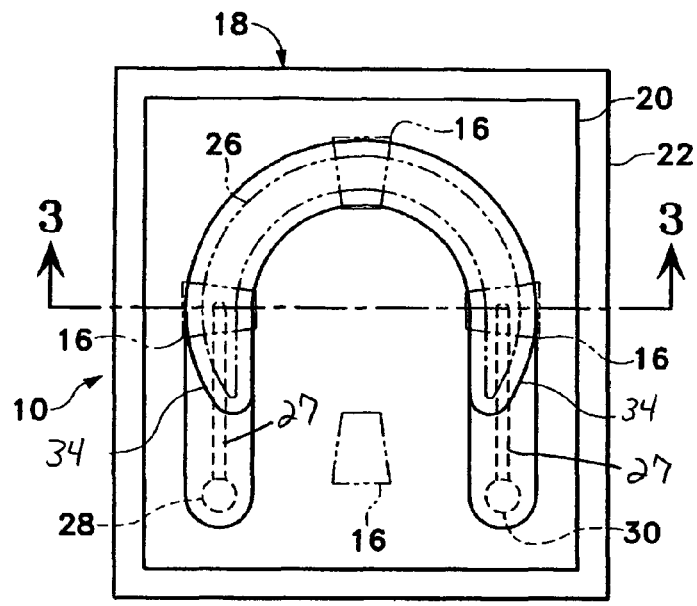
FIG. 1 is a schematic top plan view of the peristaltic pump of the cassette of the present invention, with the motor and roller head removed for clarity.
Figure 2:
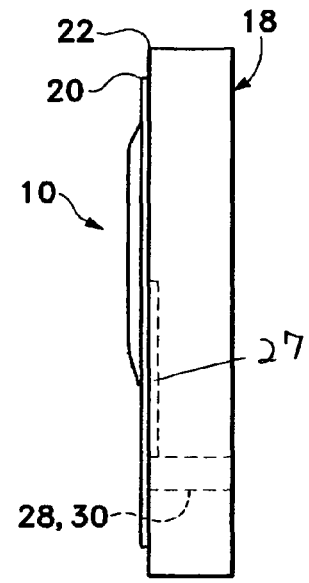
FIG. 2 is a schematic side elevational view of the peristaltic pump of the cassette of the present invention, with the motor and roller head removed for clarity.
Figure 3:
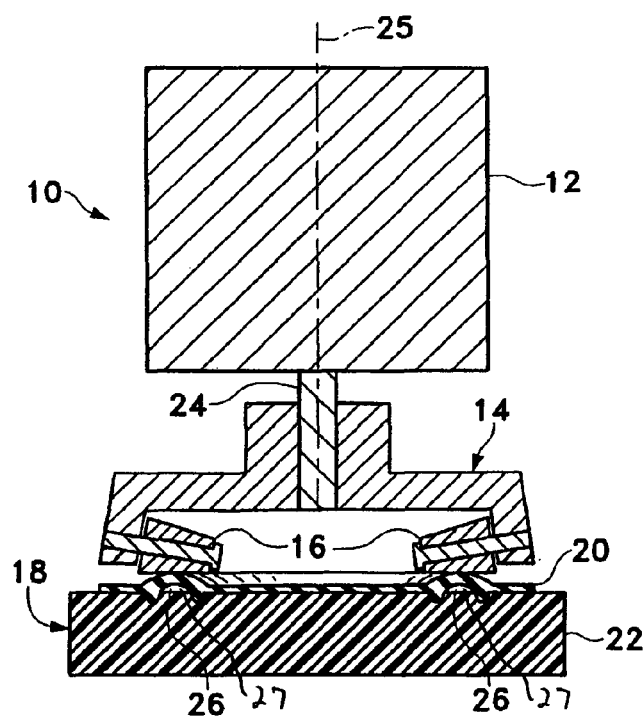
FIG. 3 is a cross-sectional view of the peristaltic pump of the cassette of the present invention taken at line 3-3 in FIG. 1.

As best seen in FIGS. 1, 2 and 3, pump 10 of the present invention generally includes pump motor 12, roller head 14, containing one or more rollers 16 and cassette 18 having elastomeric sheet 20 applied to the exterior of relatively rigid body or substrate 22. Pump motor 12 preferably is a stepper or D.C. servo motor. Roller head 14 is attached to shaft 24 of motor 12 so that motor 12 rotates roller head 14 in a plane generally normal to axis 25 of shaft 24, and the longitudinal axes of rollers 16 are generally radial to axis 25 of shaft 24.

Sheet 20 contains molded fluid channel 26 and substrate 22 contains molded fluid channel 27, that are generally arcuate in shape where fluid channel 26 meets roller head 14, with fluid channel 26 having a radius approximating that of rollers 16 about shaft 24. Fluid channels 26 and 27 fluidly connect pump inlet and pump outlet ports 28 and 30. Sheet 20 may be made of any suitably flexible, easily molded material such as silicone rubber or thermoplastic elastomer. Sheet 20 is attached or bonded to substrate 22 by any suitable technique such as adhesive, heat fusion or mechanical crimping. Substrate 22 preferably is made of a material that is rigid with respect to sheet 20, such as a rigid thermoplastic, and may be made by any suitable method, such as machining or injection molding.

In use, cassette 18 is held in close proximity to roller head 14 so that rollers 16 compress channel 26 against substrate 22 as roller head 14 rotates. The longitudinal axes of the rollers are arranged so that roller 16 contact with channel 26 is generally parallel with the plane of channel 26. Such an arrangement eliminates the need to loop a length of flexible tubing over the pump roller head and thus simplifies the loading of pump channel 26 against pump roller head 14. Rollers 16 may be tapered along their axial length to accommodate the difference in path length traveled by the inner and outer sections of rollers 16 as roller head 14 rotates.

Figure 4:
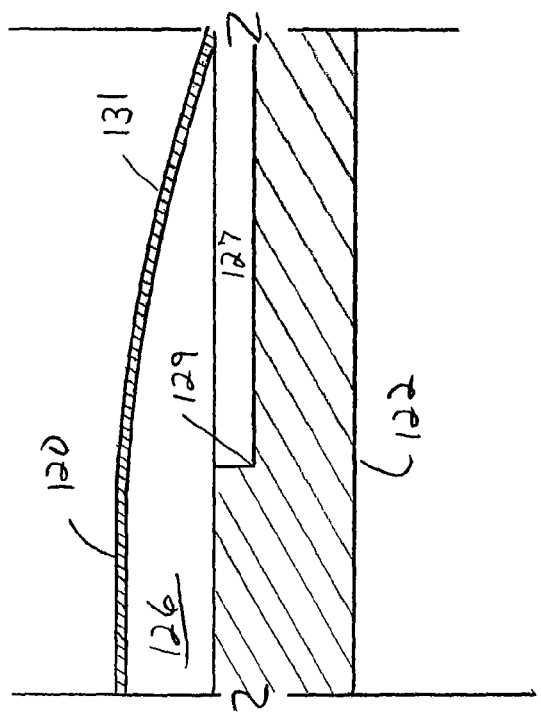
FIG. 4 is a partial cross-section view of a prior art cassette fluid channel.

As best seen in FIG. 4, prior art peristaltic pumps have an elastomeric sheet 120 adhered to relatively rigid substrate 122, forming fluid channel 126. The fluid pathway into fluid channel 126 includes fluid channel 127 that is molded into substrate 122. Fluid channel 127; however, contains relatively sharp corner 129 and other abrupt obstructions (not shown) and the cross-sectional area of fluid channel 126 varies at ramped or tapered section. 131. These features can allow some pump pulsations to enter the fluid being pumped.

Figure 5:
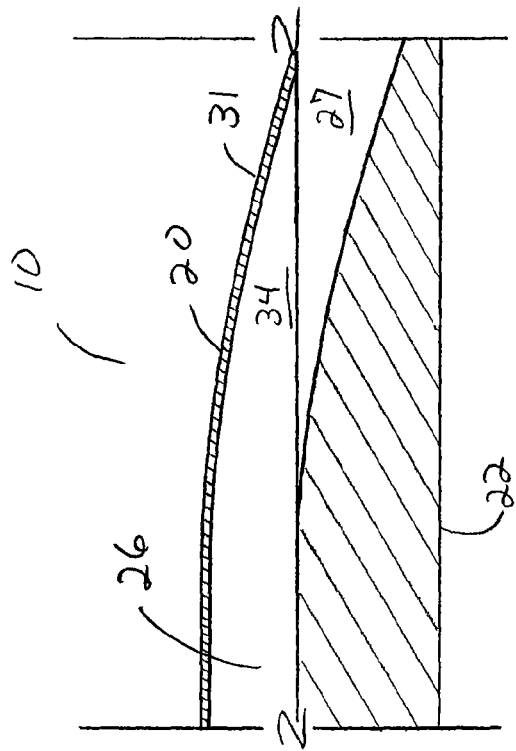
FIG. 5 is a partial cross-sectional view of the cassette fluid channel of the present invention.

As best seen in FIG. 5, substrate 22 of the present invention contains molded fluid channel 27 that provides the fluid input to fluid channel 26. Channels 26 and 27 are smoothly curving and are relatively freed from sharp edges and abrupt obstructions. The shape of channel 27 is such that it corresponds to ramped or tapered section 31 of sheet 20, so as to provide transition fluid channel region 34 between substrate 22 and sheet 20 having a relatively constant cross-sectional area that approximates the cross-sectional area of fluid channels 26 and 27. In other words, channels 26 and 27 and transition fluid channel region 34 form a constant fluid pathway in cassette 18 that is of relatively constant cross-sectional area. Such a relatively constant cross-sectional area helps prevent the introduction of pulsations in fluid channels 26 and 27 when sheet 20 is compressed against substrate 22 by rollers 16.

This description is given for purposes of illustration and explanation. It will be apparent to those skilled in the relevant art that modifications may be made to the invention as herein described without departing from its scope or spirit.

We claim:

1. A cassette, comprising:
   a) a body having an exterior;
   b) a flexible sheet attached to the body, the sheet containing at least one first molded fluid channel, the at least one first molded fluid channel projecting outwardly from the exterior of the body and wherein the flexible sheet is tapered so as to form a tapered section of the at least one first molded fluid channel; and
   c) at least one second molded fluid channel formed in the body and located so as to correspond with the tapered section of the at least one first molded fluid channel to form a transition fluid channel region, the transition fluid channel region being of relatively uniform cross-sectional area; and
   wherein the at least one first molded fluid channel and the transition fluid channel region are of approximately the same uniform cross-sectional area.

2. The cassette of claim 1 wherein the at least one first molded fluid channel and the at least one second molded fluid channel are fluidly connected to a pump inlet port.

3. The cassette of claim 1 wherein the at least one first molded fluid channel and the at least one second molded fluid channel are fluidly connected to a pump outlet port.

4. The cassette of claim 1 wherein the sheet comprises a flexible, easily molded material.

5. The cassette of claim 1 wherein the sheet comprises silicone rubber or thermoplastic elastomer.

6. The cassette of claim 1 wherein the first molded fluid channel and the second molded fluid channel are relatively freed from sharp edges and abrupt obstructions.

7. The cassette of claim 1, wherein the at least one first molded fluid channel, the at least one second molded fluid channel, and the transition fluid channel region all are of approximately the same uniform cross-sectional area.

8. A cassette, comprising:
   a) a body having an exterior;
   b) a flexible sheet attached to the body, the sheet containing at least one first molded fluid channel, the at least one first molded fluid channel projecting outwardly from the exterior of the body and wherein the flexible sheet is tapered so as to form a tapered section of the at least one first molded fluid channel; and
   c) at least one second molded fluid channel formed in the body and located so as to correspond with the tapered section of the at least one first molded fluid channel to form a transition fluid channel region, the transition fluid channel region being of relatively uniform cross-sectional area; and
   wherein the at least one first molded fluid channel and the transition fluid channel region comprise a fluid pathway that is of relatively constant cross-sectional area.

9. The cassette of claim 8 wherein the at least one first molded fluid channel and the at least one second molded fluid channel are fluidly connected to a pump inlet port.

10. The cassette of claim 8 wherein the at least one first molded fluid channel and the at least one second molded fluid channel are fluidly connected to a pump outlet port.

11. The cassette of claim 8 wherein the sheet comprises a flexible, easily molded material.

12. The cassette of claim 8 wherein the sheet comprises silicone rubber or thermoplastic elastomer.

13. The cassette of claim 8 wherein the first molded fluid channel and the second molded fluid channel are relatively freed from sharp edges and abrupt obstructions.

14. The cassette of claim 8, wherein the at least one first molded fluid channel, the at least one second molded fluid channel, and the transition fluid channel region comprise a fluid pathway that is of relatively constant cross-sectional area.

15. A surgical cassette having a body defining a rigid substrate for use in combination with a peristaltic pump having pump head rollers configured to compress an elastomeric flow channel against the rigid substrate during operation, said cassette having:
   a relatively flexible sheet attached to the exterior of the body, the sheet containing at least one channel molded in the sheet, so as to define at least one first fluid channel formed between the exterior of the body and the channel molded in the sheet, said first fluid channel defining a ramped or a tapered section; and
   at least one second fluid channel molded in the body and located so as to correspond with the at least one first fluid channel to form a transition fluid channel region where the first and second fluid channels meet;
   wherein the transition fluid channel region is formed in the body and flexible sheet with a curved slope so as to correspond with the ramped or tapered section of the first fluid channel such that the cross-sectional area of the transition fluid channel region is of relatively constant cross-sectional area over its entire length.

16. The cassette of claim 15, wherein the cross-sectional area of the transition fluid channel region approximates to the cross-sectional area of the at least one first fluid channel.

17. The cassette of claim 15, wherein the at least one first fluid channel, the at least one second fluid channel, and the transition fluid channel region all are of approximately the same uniform cross-sectional area.

18. The cassette of claim 15, wherein the at least one first fluid channel, the at least one second fluid channel, and the transition fluid channel region comprise a fluid pathway in the cassette that is of relatively constant cross-sectional area, whereby when the elastomeric flow channel is compressed against the rigid substrate during operation, introduction of fluid pressure pulsations in the flow pathway are reduced.

* * * * *